(12) United States Patent
Sanapureddy et al.

(10) Patent No.: US 8,212,025 B2
(45) Date of Patent: Jul. 3, 2012

(54) PROCESS FOR PREPARING NEVIRAPINE

(75) Inventors: Jagan Mohan Reddy Sanapureddy, Hyderabad (IN); Ramesh Dandala, Hyderabad (IN); Sivakumaran Meenakshisunderam, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 314 days.

(21) Appl. No.: 12/451,600

(22) PCT Filed: May 14, 2008

(86) PCT No.: PCT/IB2008/001249
§ 371 (c)(1),
(2), (4) Date: Nov. 21, 2009

(87) PCT Pub. No.: WO2008/142528
PCT Pub. Date: Nov. 27, 2008

(65) Prior Publication Data
US 2010/0125137 A1     May 20, 2010

(30) Foreign Application Priority Data
May 22, 2007   (IN) .......................... 1073/CHE/2007

(51) Int. Cl.
*C07D 401/12*   (2006.01)
*C07D 471/14*   (2006.01)

(52) U.S. Cl. ........................ 540/495; 546/262
(58) Field of Classification Search ............... 540/495; 546/262
See application file for complete search history.

(56) References Cited

U.S. PATENT DOCUMENTS 5,366,972 A * 11/1994 Hargrave et al. .............. 514/220
5,569,760 A * 10/1996 Schneider et al. ............. 540/495

* cited by examiner

*Primary Examiner* — Bruck Kifle
(74) *Attorney, Agent, or Firm* — Jay R. Akhave

(57) ABSTRACT

An improved process for preparing 11-cyclopropyl-5,11-dihydro-4-methyl-6H-dipyrido[3,2-b:2',3'-e][1,4]diazepin-6-one of Formula (I).

(I)

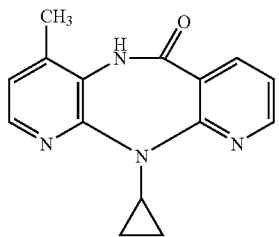

11 Claims, No Drawings

PROCESS FOR PREPARING NEVIRAPINE

FIELD OF THE INVENTION

The present invention relates to an improved process for preparing 11-cyclopropyl-5,11-dihydro-4-methyl-6H-dipyrido[3,2-b:2',3'-e] [1,4]diazepin-6-one of Formula I,

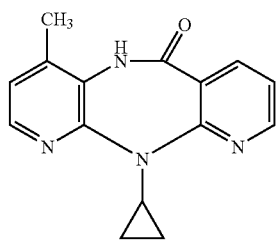

(I)

BACKGROUND OF THE INVENTION

11-Cyclopropyl-5,11-dihydro-4-methyl-6H-dipyrido[3,2-b:2',3'-e][1,4]diazepin-6-one of Formula I, which is generically known as Nevirapine, is a non-nucleoside reverse transcriptase inhibitor with activity against Human Immunodeficiency Virus Type 1 (HIV-1). Nevirapine is marketed as tablets under the brand name VIRAMUNE and Nevirapine hemihydrate as oral suspension.

Nevirapine was first disclosed in U.S. Pat. No. 5,366,972. U.S. Pat. No. 5,366,972 discloses a process to prepare nevirapine, which is as summarized below:

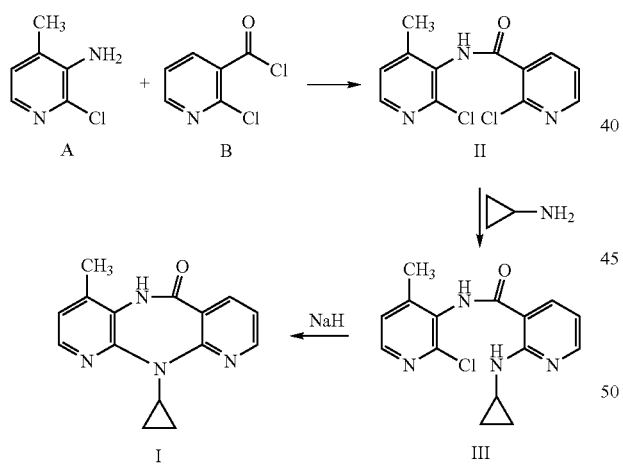

3-Amino-2-chloro-4-methylpyridine of Formula A is condensed with 2-chloronicotinoyl chloride of Formula B to give 2-chloro-N-(2-chloro-4-methyl-3-pyridinyl)-3-pyridine carboxamide of Formula II, which is then reacted with cyclopropylamine to give N-(2-chloro-4-methyl-3-pyridyl)-2 -cyclopropylamino) -3-pyridine carboxamide of Formula III. Then N-(2-chloro-4-methyl-3-pyridyl)-2-(cyclopropylamino)-3-pyridine carboxamide was cyclized in the presence of sodium hydride to give nevirapine of Formula I. The disadvantage of the above process is use of large excess of cyclopropylamine. Further, with the above process undesirable side products are obtained during the reaction, which makes the product impure.

U.S. Pat. No. 5,569,760 discloses a process for the preparation of nevirapine, which comprises, the reaction of 2-chloro-N-(2-chloro-4-methyl-3-pyridinyl)-3-pyridine carboxamide with cyclopropylamine is carried out in the presence of a neutralizing agent, which is an oxide or hydroxide of an element of the second main or second subgroup of the periodic table. Calcium oxide is used preferably.

Surprisingly, it has now been found that the large excess of the relatively expensive cyclopropylamine may be reduced if the reaction is carried out in the presence of a reagent such as potassium fluoride or trisodium phosphate dodecahydrate.

OBJECTIVE

The objective of the present invention is to provide an improved process for preparing nevirapine with good quality and purity.

In yet another objective of the present invention is to provide an improved process for preparing nevirapine, which is simple, industrially applicable and economically viable.

SUMMARY OF THE INVENTION

The present invention relates to an improved process for preparing 11-cyclopropyl-5,11-dihydro-4-methyl-6H-dipyrido[3,2-b:2',3'-e][1,4]diazepin-6-one of Formula I,

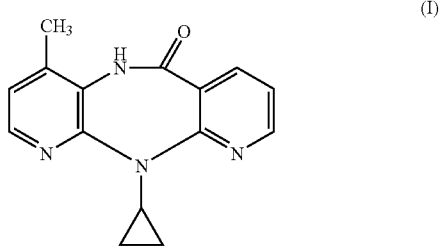

(I)

which comprises:
a) reacting 2-chloro-N-(2-chloro-4-methyl-3-pyridinyl)-3-pyridine carboxamide of Formula II,

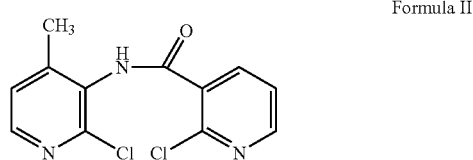

Formula II with cyclopropylamine in the presence of a reagent such as potassium fluoride or trisodium phosphate dodecahydrate and solvent to give N-(2-chloro-4-methyl-3-pyridyl)-2-(cyclopropylamino)-3-pyridine carboxamide of Formula III,

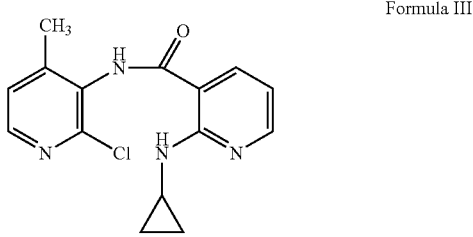

Formula III b) cyclizing the compound of Formula III to produce nevirapine;

c) isolating the nevirapine of Formula I.

DETAILED DESCRIPTION OF THE INVENTION

The process for preparing nevirapine by reacting 2-chloro-N-(2-chloro-4-methyl-3-pyridinyl)-3-pyridine carboxamide of Formula II with cyclopropylamine in the presence of a reagent such as potassium fluoride or trisodium phosphate dodecahydrate and a solvent to give N-(2-chloro-4-methyl-3-pyridyl)-2-(cyclopropylamino)-3-pyridine carboxamide of Formula III, which is then cyclized in the presence of metallating agent and a solvent to give nevirapine. The metallating agent such as lithium, sodium and potassium hydrides or lithium alkyls such as n-butyl lithium and a solvent for cyclization in an inert solvent such as tetrahydrofuran, 1,4-dioxane, glycoldimethyl ether, diethylene-glycoldimethyl ether, triethyleneglycoldimethyl ether, dimethylformamide, pyridine, xylene, benzene or anisole; dipolar aprotic solvents such as sulfolane or dimethylsulfone. The solvent used for preparing N-(2-chloro-4-methyl-3-pyridyl)-2-(cyclopropylamino)-3-pyridine carboxamide is selected from open chain or cyclic ethers, such as tetrahydrofuran, 1,4-dioxane, glycoldimethyl ether, diethyleneglycoldimethyl ether; aromatic hydrocarbons, such as benzene, toluene, xylene, chlorobenzene or pyridine; alcohols such as methanol, ethanol, isopropanol; dipolar aprotic solvents, such as dimethylformamide; 1,3-dimethyl-2-imidazolidinone, 1,3-dimethyltetrahydro-2 (1H)-pyrimidinone and sulfolane. Potassium fluoride and trisodium phosphate dodecahydrate are used to trap the acid formed during the reaction.

The 2-Chloro-N-(2-chloro-4-methyl-3-pyridinyl)-3-pyridine carboxamide of Formula II is prepared using the methods known in prior-art.

The present invention also comprises, further conversion of isolated nevirapine to its hydrates thereof.

The invention is illustrated with the following examples, which are provided by way of illustration only and should not be construed to limit the scope of the invention.

EXAMPLE 1

Preparation of N-(2-chloro-4-methyl-3-pyridyl)-2-(cyclopropylamino)-3-pyridine carboxamide 2-Chloro-N-(2-chloro-4-methyl-3-pyridinyl)-3-pyridine carboxamide (10 g), potassium fluoride (6.17 g), cyclopropylamine (8.08 g) were suspended in o-xylene (30 ml) and heated to 130-140° C. in autoclave for 5-6 h. Then the reaction mass was cooled to 25-30° C., diluted with o-xylene (50 ml) and further heated the reaction mass to 70-75° C. Thereafter, DM water (30 ml), added and stirred for 10 min at 70-75° C. The aqueous layer was separated at hot condition and organic layer was washed with DM water (30 ml) at 70-75° C. and organic layer was concentrated at 60-63° C. under reduced pressure. The concentrated mass was cooled to 25-30° C. and stirred for 15 min and further cooled to 5-10° C. and stirred for 30 min. Filtered the solid obtained and washed with chilled o-xylene (10 ml, 5-10° C.). Dried the obtained solid at 45-50° C. under reduced pressure.

Yield—9.85 g

HPLC purity—99.28%

EXAMPLE 2

Preparation of N-(2-chloro-4-methyl-3-pyridyl)-2-(cyclopropylamino)-3-pyridine carboxamide 2-Chloro-N-(2-chloro-4-methyl-3-pyridinyl)-3-pyridine carboxamide (100 g), potassium fluoride (22.62 g), cyclopropylamine (80.85 g) were suspended in o-xylene (300 ml) and heated to 130-140° C. in autoclave for 5-9 h. Then the reaction mass was cooled to 25-30° C., diluted with o-xylene (500 ml) and further heated the reaction mass to 70-75° C. Thereafter, DM water (300 ml) added and stirred for 10 min at 70-75° C. The aqueous layer was separated at hot condition and organic layer was washed with DM water (300 ml) at 70-75° C. and organic layer was concentrated at 60-63° C. under reduced pressure up to residue weight attained is approximately 400 g. The concentrated mass was cooled to 25-30° C. and stirred for 15 min and further cooled to 5-10° C. and stirred for 30 min. Filtered the solid obtained and washed with chilled o-xylene (100 ml, 5-10° C.). Dried the obtained solid at 50-60° C. under reduced pressure.

Yield—97 g

HPLC purity—99.85%

EXAMPLE 3

Preparation of N-(2-chloro-4-methyl-3-pyridyl)-2-(cyclopropylamino)-3-pyridine carboxamide 2-Chloro-N-(2-chloro-4-methyl-3-pyridinyl)-3-pyridine carboxamide (100 g), potassium fluoride (41.13 g), cyclopropylamine (80.85 g) were suspended in o-xylene (300 ml) and heated to 130-140° C. in autoclave for 5-9 h. Then the reaction mass was cooled to 25-30° C., diluted with o-xylene (500 ml) and further heated the reaction mass to 70-75° C. Thereafter, DM water (300 ml) added and stirred for 10 min at 70-75° C. The aqueous layer was separated at hot condition and organic layer was washed with DM water (300 ml) at 70-75° C. and organic layer was concentrated at 60-63° C. under reduced pressure up to residue weight attained is approximately 400 g The concentrated mass was cooled to 25-30° C. and stirred for 15 min and further cooled to 5-10° C. and stirred for 30 min. Filtered the solid obtained and washed with chilled o-xylene (100 ml, 5-10° C.). Dried the obtained solid at 50-60° C. under reduced pressure.

Yield—95 g

HPLC purity—99.76%

EXAMPLE 4

Preparation of N-(2-chloro-4-methyl-3-pyridyl)-2-(cyclopropylamino)-3-pyridine carboxamide 2-Chloro-N-(2-chloro-4-methyl-3-pyridinyl)-3-pyridine carboxamide (15 g), trisodium phosphate dodecahydrate (20.21 g), cyclopropylamine (12.12 g) were suspended in o-xylene (45 ml) and heated to 130-140° C. for 6-8 h in S.S. Bomb with occasional shaking. Then the reaction mass was cooled to 70-75° C., diluted with o-xylene (75 ml) and DM water (45 ml) and stirred for 10 min at 70-80° C. The aqueous layer was separated and washed the organic layer with DM water (45 ml) at 70-80° C. The organic layer was concentrated at 60-65° C. under reduced pressure. The concentrated mass was cooled to 5-10° C. and stirred for 30 min. Filtered the solid obtained and washed with chilled o-xylene (15 ml, 5-10° C.). Dried the obtained solid at 55-60° C. under reduced pressure.

Yield—14 g

HPLC purity—99%

EXAMPLE 5

Preparation of N-(2-chloro-4-methyl-3-pyridyl)-2-(cyclopropylamino)-3-pyridine carboxamide 2-Chloro-N-(2-chloro-4-methyl-3-pyridinyl)-3-pyridine carboxamide (50 g), potassium fluoride (30.85.g), cyclopropylamine (40.43 g) were suspended in o-xylene (150 ml) and heated to 130-140° C. in autoclave for 5-8 h. Then the reaction mass was cooled to 25-30° C., diluted with o-xylene (250 ml) and further heated the reaction mass to 70-75° C. Thereafter, DM water (150 ml) added and stirred for 10 min at 70-75° C. The aqueous layer was separated at hot condition and organic layer was washed with DM water (150 ml) at 70-75° C. and organic layer was concentrated at 60-63° C. under reduced pressure up to residual weight attained is approximately 200 g. The concentrated mass was cooled to 25-30° C. and stirred for 15 min and further cooled to 5-10° C. and stirred for 30 min. Filtered the solid obtained and washed with chilled o-xylene (50 ml, 5-10° C.). Dried the obtained solid at 45-50° C. under reduced pressure.

Yield—46.5 g

Assay (By HPLC)—99.9%.

EXAMPLE 6

Preparation of N-(2-chloro-4-methyl-3-pyridyl)-2-(cyclopropylamino)-3-pyridine carboxamide 2-Chloro-N-(2-chloro-4-methyl-3-pyridinyl)-3-pyridine carboxamide (50 g), trisodium phosphate dodecahydrate (67.37 g), cyclopropylamine (40.43 g) were suspended in o-xylene (150 ml) and heated to 130-140° C. for 6-8 h in autoclave. Then the reaction mass was cooled to 70-75° C., diluted with o-xylene (250 ml) and DM water (150 ml) and stirred for 10 min at 70-80° C. The aqueous layer was separated and washed the organic layer with DM water (150 ml) at 70-80° C. The organic layer was concentrated at 60-65° C. under reduced pressure up to residual weight attained is approximately 200 g. The concentrated mass was cooled to 5-10° C. and stirred for 30 min. Filtered the solid obtained and washed with chilled o-xylene (50 ml, 5-10° C.). Dried the obtained solid at 55-60° C. under reduced pressure.

Yield—46.5 g

HPLC purity—99.70%

EXAMPLE 7

Preparation of Nevirapine

Sodium hydride (9.15 g, 65% w/w) was suspended in o-xylene (187.5 ml) at 25-30° C. under nitrogen atmosphere and slowly heated to 130-135° C. N-(2-chloro-4-methyl-3-pyridyl)-2-(cyclopropylamino)-3-pyridine carboxamide (25 g) was dissolved in diglyme (50 ml) at 70-80° C. and added to the above suspension over a period of 10-20 min at 135-138° C. and stirred for 1 h at 135-140° C. Thereafter the reaction mixture was cooled to 5° C. and acetic acid (8.75 ml) was added slowly below 15° C. Then cold DM water (100 ml) was added to the reaction mixture slowly below 15° C. and pH of the reaction mixture was adjusted to 6.5 using acetic acid (4.25 ml) at 5-10° C. The temperature of the reaction mixture was raised to 20-25° C. and stirred for 1 h at 20-25° C. and product crystallizes out. The product obtained was filtered and washed with DM water (75 ml) and then with cyclohexane (50 ml) and suck dried the product under suction for 10 min. The wet product (27.5 g) was suspended in a mixture of methanol (750 ml) and DM water (175 ml) and heated to reflux at 70° C., a clear solution formed. Carbon (2.5 g) was added and stirred for 30 min at reflux. Filtered the carbon in hot condition and washed with hot methanol (50 ml, 60-65° C.). Filtrate was concentrated under reduced pressure at 50-55° C. up to residual weight attained is approximately 225 g. Thereafter cooled the concentrated mass to 5-10° C. and stirred for 30 min at 5-10° C. The product obtained was filtered and washed with cold DM water (25 ml, 5-10° C.), suck dried and dried at 65-70° C. under reduced pressure.

Yield—17.5 g

HPLC purity—99.92%

Moisture content—0.08% w/w

EXAMPLE 8

Preparation of Nevirapine Hemihydrate

Anhydrous nevirapine (75 g) was suspended in DM water (300 ml) at 20-25° C. The reaction mass was cooled to 18-22° C. and conc. HCl (86 ml) was added over a period of 10 min below 30° C. Thereafter the reaction mixture was stirred for 5 min at 25-30° C., a clear solution was formed. Carbon (3.75 g) was added to the reaction mixture and stirred for 15 min at 23-25° C. and filtered the carbon and washed with DM water (75 ml, 20-25° C.). The pH of filtrate was adjusted to 6.72 using 20% w/w aqueous sodium hydroxide solution at 25-30° C. and cooled to 15-20° C. and stirred for 30 min and product crystallizes out. The product so obtained was filtered and washed with DM water (2×112.5 ml, 20-25° C.), suck dried and dried under reduced pressure at 40-45° C. till moisture is 3.1-3.9% w/w.

Yield: 74.45 g

HPLC purity—99.96%

Moisture content—3.54% w/w

We claim:

1. A process for preparing N-(2-chloro-4-methyl-3-pyridyl)-2-(cyclopropylamino)-3-pyridine carboxamide of Formula III,

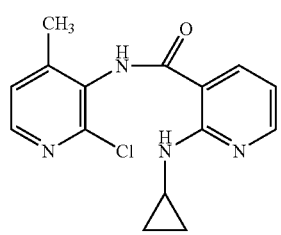

Formula III which comprises:
   a) reacting 2-chloro-N-(2-chloro-4-methyl-3-pyridinyl)-3-pyridine carboxamide of Formula II,

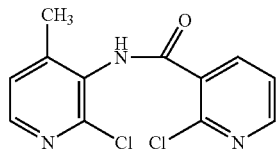

Formula II with cyclopropylamine in the presence of potassium fluoride or trisodium phosphate dodecahydrate and solvent to give N-(2-chloro-4-methyl-3-pyridyl)-2-(cyclopropylamino)-3-pyridine carboxamide of Formula III,

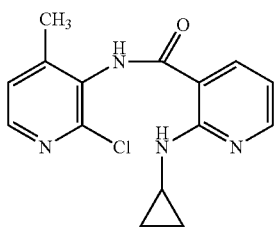

Formula III b) cyclizing the compound of Formula III to produce nevirapine; and
   c) isolating the nevirapine of Formula I.

6. The process according to claim 5, wherein the solvent used for preparing N-(2-chloro-4-methyl-3-pyridyl)-2-(cyclopropylamino)-3-pyridine carboxamide is selected from open chain or cyclic ethers selected from the group consisting of tetrahydrofuran, 1,4-dioxane, glycoldimethyl ether and diethyleneglycoldimethyl ether; aromatic hydrocarbons selected from the group consisting of benzene, toluene, xylene, chlorobenzene and pyridine; alcohols selected from the group consisting of methanol, ethanol, isopropanol; dipolar aprotic solvents selected from the group consisting of dimethylformamide, 1,3-dimethyl-2-imidazolidinone, 1,3-dimethyltetrahydro-2(1H)-pyrimidinone, sulfolane and mixtures thereof.

7. The process according to claim 5, wherein cyclization is carried out using a metallating agent and a solvent.

8. The process according to claim 6, wherein metallating agent is selected from the group consisting of lithium, sodium and potassium hydrides and n-butyl lithium.

9. The process according to claim 5, wherein the solvent for cyclization is selected from the group consisting of tetrahydrofuran, 1,4-dioxane, glycoldimethyl ether, diethylene-glycoldimethyl ether, triethyleneglycoldimethyl ether, dimethylformamide, pyridine, xylene, benzene and anisole; dipolar aprotic solvents selected from the group consisting of sulfolane and dimethylsulfone and mixtures thereof.

10. The process according to claim 5, wherein the nevirapine is isolated as a base or hydrates thereof.

11. The process according to claim 4, wherein the nevirapine is isolated as a base or hydrates thereof.

* * * * * with cyclopropylamine in the presence of potassium fluoride or trisodium phosphate dodecahydrate and solvent.

2. The process according to claim 1, wherein the solvent used for preparing N-(2-chloro-4-methyl-3-pyridyl)-2-(cyclopropylamino)-3-pyridine carboxamide is selected from open chain or cyclic ethers selected from the group consisting of tetrahydrofuran, 1,4-dioxane, glycoldimethyl ether and diethyleneglycoldimethyl ether; aromatic hydrocarbons selected from the group consisting of benzene, toluene, xylene, chlorobenzene and pyridine; alcohols selected from the group consisting of methanol, ethanol and isopropanol; dipolar aprotic solvents; 1,3-dimethyl-2-imidazolidinone, 1,3-dimethyltetrahydro-2(1H)-pyrimidinone, sulfolane and mixtures thereof.

3. The process according to claim 2, wherein the solvent is xylene.

4. The process according to claim 1, wherein N-(2-chloro-4-methyl-3-pyridyl)-2-(cyclopropylamino)-3-pyridine carboxamide of Formula III is further converted to nevirapine or hydrates thereof.

5. A process for preparing 11-cyclopropyl-5,11-dihydro-4-methyl-6H-dipyrido[3,2-b:2',3'-e][1,4]diazepin-6-one of Formula I,

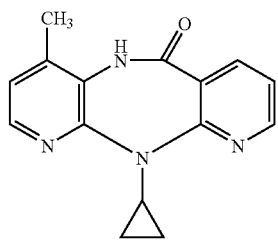

(I)

which comprises:
   a) reacting 2-chloro-N-(2-chloro-4-methyl-3-pyridinyl)-3-pyridine carboxamide of Formula II,

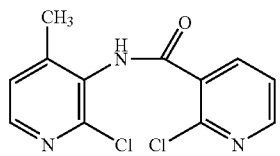

Formula II